United States Patent

Giroldini et al.

[11] Patent Number: 4,497,739
[45] Date of Patent: Feb. 5, 1985

[54] SYNTHESIZING THIOCARBAMIC ACID ESTERS

[75] Inventors: Villiam Giroldini; Carlo Neri, both of S. Donato Milanese, Italy

[73] Assignee: Anic S.p.A., Palermo, Italy

[21] Appl. No.: 463,553

[22] Filed: Feb. 3, 1983

[30] Foreign Application Priority Data

Feb. 9, 1982 [IT] Italy .............................. 19518 A/82

[51] Int. Cl.³ .................. C07C 155/02; C07D 213/02
[52] U.S. Cl. ........................ 260/239 BF; 260/455 A; 564/63
[58] Field of Search .......... 260/455 A, 239 BF, 239 B

[56] References Cited

U.S. PATENT DOCUMENTS 3,732,272  5/1973  Tilles .............................. 260/455 A Primary Examiner—Henry R. Jiles
Assistant Examiner—Robert C. Whittenbaugh
Attorney, Agent, or Firm—Hedman, Gibson, Costigan & Hoare

[57] ABSTRACT

A process for the synthesis of thiocarbamic acid esters by reacting amine compounds having a general formula

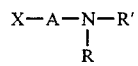

wherein A is an arylene radical, simple or substituted by halogens hydrocarbon radicals, alkoxy groups, or can be an alkylene radical having from 1 to 15 carbon atoms, straight-line or branched, simple or substituted, whereas X can be hydrogen —$NH_2$ or can be an $H_2$—N—Z group in which the bivalent function Z derives from alkyl, aryl, cycloaryl, alkaryl, aralkyl radicals which can be, in their turn, simple or substituted, R and R' equal or different can be hydrogen or alkyl, aryl, alkaryl radicals and otherwise, with carbon monoxide, in the presence of a catalyst composed of a metallic selenide. The thiocarbamic acid esters are known compounds that find applications as medicaments for plants and as intermediates for organic synthesis.

13 Claims, No Drawings

SYNTHESIZING THIOCARBAMIC ACID ESTERS

This invention relates to a process for the synthesis of thiorcarbamic acid esters by carbonylation with carbon monoxide of primary and secondary amines and organic disulphides, in the presence of metallic selenides as catalysts.

The primary and secondary amines to be used have the general formula

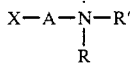

wherein A is an arylene radical, unsubstituted or substituted with halogens, hydrocarbons radicals, alkoxy groups or can be an alkylene radical having from 1 to 15 carbon atoms, straight line or branched, unsubstituted or substituted whereas X can be hydrogen, $-NH_2$ or can be a group $H_2N-Z$ in which the bivalent function Z derives from alkyl, aryl, cycloalkyl, alkaryl and aralkyl radicals, which in their turn can be unsubstituted or substituted, and R and R', equal or different, can be hydrogen or alkyl, aryl, alkaryl radicals and otherwise.

The importance of the thiocarbamic acid esters is known as they find applications as medicaments for plants and intermediates for important organic synthesis.

The thiocarbamic esters are prepared, at present, principally with any of the three following methods, viz.:

1. Reaction between an isocyanate and a mercaptan according to the reaction pattern:

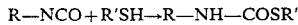

2. Reaction between an amine and a chlorothiocarbonate, according to the pattern:

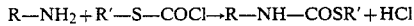

These synthesis involve considerable disadvantages in operation as they start from expensive products which are difficult to be prepared.

3. Reaction between a primary amine, carbon disulphide and monoxide in the presence of elemental selenium as the catalyst (Italian Pat. No. 1037678).

The latter reaction is a considerable simplification in the synthesis of thiocarbamates over the two previous methods. There is the drawback, however, that the latter method produces by-products which are a liability in connection with the purification of the end products.

It has now been found, and this is the subject matter of the present invention, that by reacting primary and secondary amines with carbon monoxide and an organic disulphide in the presence of metallic selenides as the catalysts, it becomes possible to obtain high-purity thiocarbamates.

More particularly, the present invention relates to the preparation of thiocarbamic acid esters starting from amine compounds corresponding to the general formula which has been reported above.

Such amine compounds are caused to react with organic disulphides having the formula $R''-S-S-R'''$ wherein R'' and R''', equal to or different from one another, are hydrocarbon radicals of the aliphatic or the aromatic species, and carbon monoxide, in the presence of catalyst systems based on metallic selenides.

The metallic selenides which lend themselves to that purpose are selected from the group consisting of: $CuSe$, $ZnSe$, $SnSe$, $SnSe_2$, $CoSe$, $NiSe$, $FeSe$, $VOSe$, $V_2Se_3$, $MnSe$, $MoSe_3$, $WSe_3$, $Sb_2Se_3$, $TiSe_2$, $CrSe_3$, $Ru_2Se_3$, $Rh_2Se_3$, $PdSe$, and $PtSe_2$.

The reaction is carried out by dissolving in an appropriate solvent (ThF, $CH_3CN$, DMF, dioxan, benzene, toluene, methanol, ethanol) the amine compound, the disulphide concerned, the catalyst, and organic base (such as triethylamine, piridine, quinoline) and the mercaptan corresponding to the disulphide which is used.

The organic base and the mercaptan act as cocatalysts.

The carbon monoxide is added under pressures which are variable between 1 and 200 atm and preferably the working pressures are between 5 and 30 atm.

The reaction temperature may be varied between 0° C. and 180° C. as a function of the kind of amine adopted.

More particularly, there have proven to be especially recommendable, on account of their stability, activity, selectivity, possibility of recycling and the purity of the final thiocarbamates, the following selenides: $CuSe$, $NiSe$, $SnSe_2$, ($VOSe$).

The molar ratio of the catalyst to the amine may be varied between 1:1000 and 1:10, the preferred range being comprised between 1:100 and 1:20 in order that an acceptable reaction velocity may be obtained.

The catalyst can be either partially or totally soluble in the reaction medium, but, on completion of the reaction, once that the solvent has been distilled off, it becomes possible to recover the catalyst integrally merely by filtration.

More particularly, with the primary aliphatic and aromatic amines, the working temperatures are comprised between 20° C. and 70° C., whereas for the secondary amines, the working temperatures are comprised between 120° C. and 170° C.

During progress of the reaction the mercaptan concerned is formed in stoichiometric proportions and it can be oxidized to the corresponding disulphide again directly in the reaction environment as such. The end products are isolated from the raw material produced by the reaction by distillation or by recrystallization, and the catalyst is recycled.

The following examples, intended to illustrate the invention without limiting same, show the process according to the present invention for obtaining the thiocarbamates.

EXAMPLE 1

A 200-ml steel autoclave is charged with 8.2 mls of aniline (90 millimols (mM)), 10 mls of dimethyldisulphide, 10 mls of triethylamine, 40 mls of $CH_3CN$, 3.1 g (grams) of $CH_3SH$ and 0.3 g of $SnSe_2$. The reaction mixture is brought to a temperature of 60° C. with stirring whereafter carbon monoxide is fed under a pressure of 25 atm. As the pressure drops to 20 atm, carbon monoxide is fed again until attaining the pressure of 25 atm again.

This operation is repeated a number of times.

After 5 hours the reaction is discontinued.

The GLC (Gas-Liquid Chromatographic) analysis of the raw product of the reaction gives the following results:

Aniline: 5 mM (millimols)
N-phenyl-S-methylthiocarbamate: 77.5 mM
N,N-biphenylurea: 3.3 mM The conversion rate is as high as 94.4% and the selectivity is 92%. The solvent is evaporated off from the raw product of the reaction under reduced pressures, whereafter the residue is dissolved again in a solvent (benzene, toluene) and filtration is carried out to collect the insolubles, among which also the catalyst, whereupon the expected product is isolated by recrystallization.

The thus prepared N-phenyl-S-methylthiocarbamate has a m.p. 82° C.

EXAMPLE 2

A 200-ml autoclave is charged with 8 mls of isopropylamine (93 mM), 10 mls of dimethylsulphide, 10 mls of triethylamine, 60 mls of $CH_3CN$, 4 g of $CH_3SH$ and 0.3 g of NiSe. The reaction mixture is brought to a temperature of 35° C. with stirring, whereupon CO is fed under a pressure of 25 atm, just after the procedure of Example 1. After 2.5 hours the reaction is halted and the contents is analyzed by GLC (Gas-Liquid Chromatography). There are obtained:

N,N'-diisopropylurea: 5.5 mM
N,N-isopropyl-S-methylthiocarbamate: 80 mM

The conversion for the amine is 98% and the selectivity is 88%. The raw product of the reaction is distilled under a low pressure to drive off the solvent, whereafter the residue is taken up with toluene, the insoluble residues are filtered off and toluene is evaporated off, so that N-isopropyl-S-methylthiocarbamate is obtained, having a m.p. of 71° C.

EXAMPLE 3

A 200-ml autoclave is charged with 8.0 mls of isopropylamine (92 mM), 10 mls of dimethyldisulphide, 10 mls of triethylamine, 60 mls of $CH_3CN$, 3.5 g of $CH_3SH$ and 0.4 g of $Sb_2Se_3$.

The mixture is brought to a temperature of 35° C. with stirring, whereafter CO is fed under a pressure of 25 atm and the procedure is the same as in the previous examples, after 1.5 hours the reaction is halted. The GLC-analysis of the reaction raw product gives the following results:

isopropylamine: 15 mM
N,N-diisopropylurea: 10.4 mM

The conversion is 84% and the selectivity is 72.5%.
The purification of the product is effected after the procedure of Example 2.

EXAMPLE 4

A 200-ml autoclave is charged with 8.2 mls (90 mM) of aniline, 10 mls of dimethylsulphide, 10 mls of pyridine, 40 mls of $CH_3CN$, 3.5 g of $CH_3SH$ and 0.4 g of ZnSe.

The reaction mixture is brought to 55° C. with stirring, whereafter CO is charged under a pressure of 25 atm, according to the procedure described previously. After 2.5 hours the reaction is discontinued and the contents of the autoclave is GLC-analyzed. The results are:

N,N-biphenylurea: 1.2 mM
Aniline: 2 mM
N-phenyl-S-methylthiocarbamate: 85.3 mM

Conversion is 98% and selectivity is 97%.
The pure product is isolated from the reaction raw material according to the procedure described in Example 1.

EXAMPLE 5

A 200-ml autoclave is charged with 9 mls of nor.-butylamine (90 mM), 10 mls of dimethyldisulphide, 10 mls of triethylamine, 40 mls of $CH_3CN$, 4.0 g of $CH_3Sh$ and 0.4 g of FeSe. The reaction mixture is brought to the temperature of 35° C. with stirring, whereafter CO is fed under a pressure of 25 atm. After 2 hours the reaction is over and the contents of the autoclave GLC-analyzed. The results are:

N,N'-dibutylurea: 5 mM
N-butyl-S-methylthiocarbamate: 73 mM

Conversion is as high as 99% and selectivity is 88.6%.
The reaction raw material is evaporated under a law pressure to drive the solvents off, whereafter the residue is dissolved in nor.hexane and the solid catalyst is filtered off.

By fractional distillation of the solution in hexane, the N-butyl-S-methylthiocarbamate is recovered.
m.p.=35° C.–b.p.=105° C.–107° C. under 10 mmHg (millimeters of mercury).

EXAMPLE 6

A 200-ml autoclave is charged with 9 mls of nor.-butylamine (90 mM), 10 mls of dimethylsulphide, 10 mls of pyridine, 40 mls of $CH_3CN$, 4.0 g of $CH_3SH$ and 0.4 g of CuSe.

The reaction mixture is brought to the temperature of 30° C. with stirring, whereafter CO is charged under a pressure of 25 atm. After 4 hours the reaction is completed and the product thus obtained is GLC-analyzed. The results are:

N,N'-dibutylurea: 4 mM
N-butyl-S-methylthiocarbamate: 81 mM

The conversion is 99% and the selectivity is as high as 91%.
The thiocarbamate is question is purified by distillation, as in Example 5.

EXAMPLE 7

A 200-ml autoclave is charged with 10 mls of hexamethylimine (90 mM), 10 mls of dimethylsulphide, 10 mls of pyridine, 50 mls of $CH_3CN$, 3.5 g of $CH_3SH$ and 0.4 g of $SnSe_2$.

The reaction mixture is brought to a temperature of 140° C. with stirring, whereupon CO is charged under a pressure of 25 atm.

The reaction is completed within 3 hours and the raw product of the reaction is analyzed.

There are obtained 60 mM of N-hexamethylene-S-methylthiocarbamate and by-products consisting of N,N'-hexamethyleneurea and N-hexamethyleneformamide. The conversion is 95% and the selectivity is 67%. The raw product of the reaction, after that the catalyst has been filtered off, is subjected to fractional distillation.

The thiocarbamate distills at the temperature of 95° C. under a pressure of 20 mmHg (millimeters of mercury).

EXAMPLE 8

A 200-ml autoclave is charged with 16.4 mls of nor.-propylamine (0.2 mol), 20 mls of dimethylsulphide, 10 mls of pyridine, 50 mls of $CH_3CN$, 0.5 g of $CH_3SH$ and 0.4 g of CuSe.

The reaction mixture is brought to a temperature of 40° C. with stirring, whereafter CO is charged under a pressure of 25 atm. The reaction is over in 4 hours and the raw product of the reaction is GLC-analyzed, the following results being obtained:

N,N'-propylurea: 12 mM
N-propyl-S-methylthiocarbamate: 174 mM (conversion 99% and selectivity 88%)

The carbamate is purified by fractionally distilling the raw product.

The product of the reaction distills at 106° C. under 20 mmHg.

We claim:

1. A process for the preparation of esters of thiocarbamic acids comprising the step of reacting carbon monoxide and organic disulphides having the formula R''—S—S—R''', wherein R'' and R''', are equal to or different from one another, are aliphatic or aromatic hydrocarbon radicals, with amine compounds having the general formula:

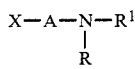

wherein R and $R^1$, are equal to or different from one another, and can be hydrogen, alkyl, aryl, or alkaryl radicals with the proviso that at least one of R and $R^1$ is hydrogen, A is an unsubstituted arylene radical, or an arylene radical that is substituted with halogens, hydrocarbon radicals, alkoxy groups or a straight or branched chain alkylene radical having from 1 to 15 carbon atoms; and X is hydrogen, —$NH_2$, or $H_2N$—Z in which the bivalent function Z is phenylene or $C_{1-4}$ alkylene in the presence of a catalyst consisting of a metallic selenide.

2. Process for the preparation of thiocarbamic acid esters according to the preceding claim characterized in that the reaction is carried out in the presence of an organic base and of a mercaptan.

3. Process for the preparation of thiocarbamic acid esters according to the preceding claims characterized in that the reaction is carried out at a temperature variable in the range from 0° C. to 180° C.

4. Process for the preparation of thiocarbamic acid esters according to claim 1, wherein the reaction is carried out with a ratio of the catalyst to the amine compound variable from 1:1000 to 1:10.

5. Process for the preparation of thiocarbamic acid esters according to claim 4 wherein the reaction is carried out with a ratio of the catalyst to the amine compound in the range between 1:100 and 1:20.

6. Process for the preparation of thiocarbamic acid esters according to claim 1, wherein the catalyst is preferably selected from the group consisting of CuSe, NiSe, and $SnSe_2$.

7. A process as defined in claim 1 wherein the ester of thiocarbamic acid is N-phenyl-S-methylthiocarbamate.

8. A process as defined in claim 1 wherein the ester of thiocarbamic acid is N-isopropyl-S-methylthiocarbamate.

9. A process as defined in claim 1 wherein the ester of thiocarbamic acid is N-butyl.

10. A process as defined in claim 1 wherein the thiocarbamic acid ester is N-hexamethylene-S-methylthiocarbamate.

11. A process as defined in claim 1 wherein the thiocarbamic acid ester is N-propyl-S-methylthiocarbamate.

12. A process for the preparation of esters of thiocarbamic acids having the general formula

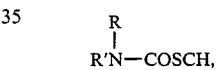

wherein R is phenyl or $C_{1-4}$ alkyl and R' is hydrogen or R' and R taken together with the N atom form a hexamethylene group, said process comprising reacting a primary amine of the formula $RNH_2$ wherein R is as above described; or hexamethylimine with dimethylsulfide and carbon monoxide with a metallic selenide catalyst and a cocatalyst consisting of methylmercaptan and an organic base which is a member selected from the group consisting of triethylamine, pyridine and guinoline at a temperature of from 20°–170°.

13. A process as defined in claim 12 wherein a primary amine of the formula $RNH_2$ and a temperature of 20° C.–70° C. is employed.

* * * * *